US011000660B2

(12) United States Patent
Goulitski et al.

(10) Patent No.: US 11,000,660 B2
(45) Date of Patent: May 11, 2021

(54) OXYGEN-CAPNOGRAPHY MASK FOR CONTINUOUS CO2 MONITORING

(71) Applicant: Oridion Medical 1987 Ltd., Jerusalem (IL)

(72) Inventors: Konstantin Goulitski, Jerusalem District (IL); Michael Kertser, Jerusalem District (IL)

(73) Assignee: ORIDION MEDICAL 1987 LTD., Jerusalem (IL)

( * ) Notice: Subject to any disclaimer, the term of this patent is extended or adjusted under 35 U.S.C. 154(b) by 756 days.

(21) Appl. No.: 15/670,877

(22) Filed: Aug. 7, 2017

(65) Prior Publication Data

US 2018/0043121 A1    Feb. 15, 2018

Related U.S. Application Data

(60) Provisional application No. 62/373,170, filed on Aug. 10, 2016.

(51) Int. Cl.
*A61M 16/06* (2006.01)
*A61M 16/08* (2006.01)
(Continued)

(52) U.S. Cl.
CPC ....... *A61M 16/0605* (2014.02); *A61B 5/0836* (2013.01); *A61B 5/097* (2013.01);
(Continued)

(58) Field of Classification Search
CPC ................ A61M 16/085; A61M 16/06; A61M 16/0833; A61M 16/0666; A61B 5/097
See application file for complete search history.

(56) References Cited

U.S. PATENT DOCUMENTS

2008/0196715 A1   8/2008   Yamamori
2008/0319334 A1  12/2008   Yamamori
(Continued)

FOREIGN PATENT DOCUMENTS

| EP | 2275031 A1 | 1/2011 |
| EP | 2859845 A1 | 4/2015 |
| WO | 2006039788 A1 | 4/2006 |

OTHER PUBLICATIONS

International Search Report for PCT Application No. PCT/IL2017/050885 dated Oct. 30, 2017, 4 pgs.
(Continued)

*Primary Examiner* — Margaret M Luarca
(74) *Attorney, Agent, or Firm* — Cantor Colburn LLP

(57) ABSTRACT

A face mask for delivering oxygen to, and sampling carbon dioxide exhaled from, a subject includes a partition wall that divides the mask into a subject respiratory space that primarily contains carbon dioxide exhaled by the subject, and an oxygen reservoir space that primarily contain oxygen. The partition wall includes one or two holes to which naris conduits are respectively connected. The naris conduit are positioned in proximity to the subject's nares to closely obtain carbon dioxide samples. The naris conduits enable oxygen to flow from the oxygen reservoir space to the subject respiratory space during inhalation, while quickly expelling traces of CO2, and they configured such that exhaled CO2 quickly fills them up, during exhalation, and while expelling oxygen traces back to the oxygen reservoir space. During exhalation.

20 Claims, 11 Drawing Sheets

(51) Int. Cl.
    *A61B 5/083*     (2006.01)
    *A61B 5/097*     (2006.01)
    *A61M 16/20*     (2006.01)

(52) U.S. Cl.
    CPC ........ *A61M 16/06* (2013.01); *A61M 16/0666* (2013.01); *A61M 16/0683* (2013.01); *A61M 16/085* (2014.02); *A61M 16/0816* (2013.01); *A61M 16/204* (2014.02); *A61M 16/205* (2014.02); *A61M 2016/0661* (2013.01); *A61M 2202/0208* (2013.01); *A61M 2202/0225* (2013.01); *A61M 2230/432* (2013.01)

(56) References Cited

U.S. PATENT DOCUMENTS

| | | | |
|---|---|---|---|
| 2011/0015534 A1* | 1/2011 | Yamamori | A61B 5/0836 600/532 |
| 2012/0289838 A1 | 11/2012 | Varga et al. | |
| 2013/0060157 A1 | 3/2013 | Beard | |
| 2013/0186406 A1* | 7/2013 | Hajgato | A61M 16/06 128/206.28 |
| 2017/0007795 A1* | 1/2017 | Pedro | A61M 16/0672 |

OTHER PUBLICATIONS

EP Application No. 17758302.8 Office Action dated May 15, 2020, 3 pages.
International Application No. PCT/IL2017/050885 International Preliminary Report on Patentability dated Feb. 12, 2019, 7 pages.

\* cited by examiner

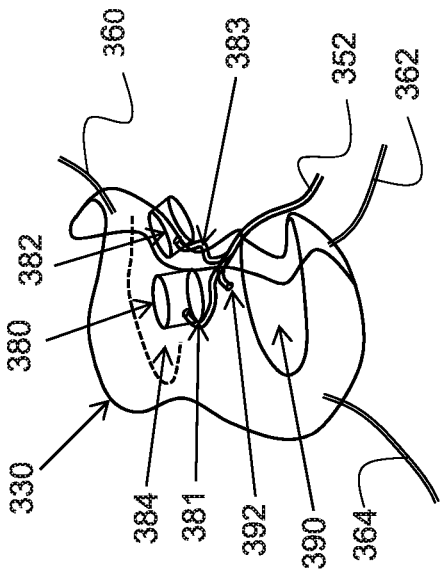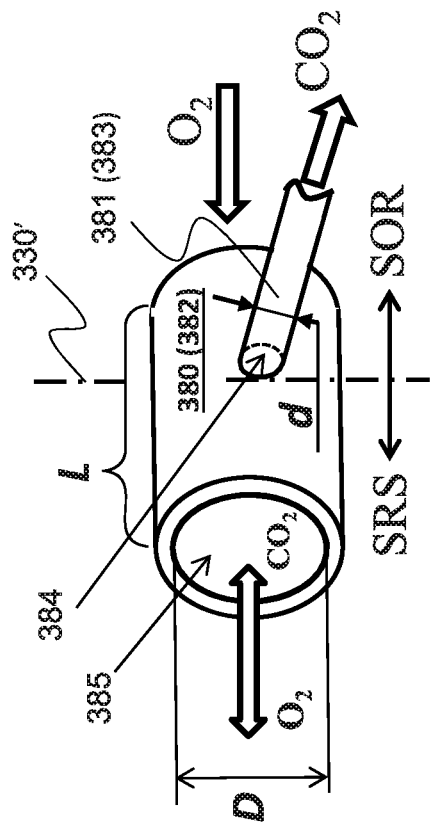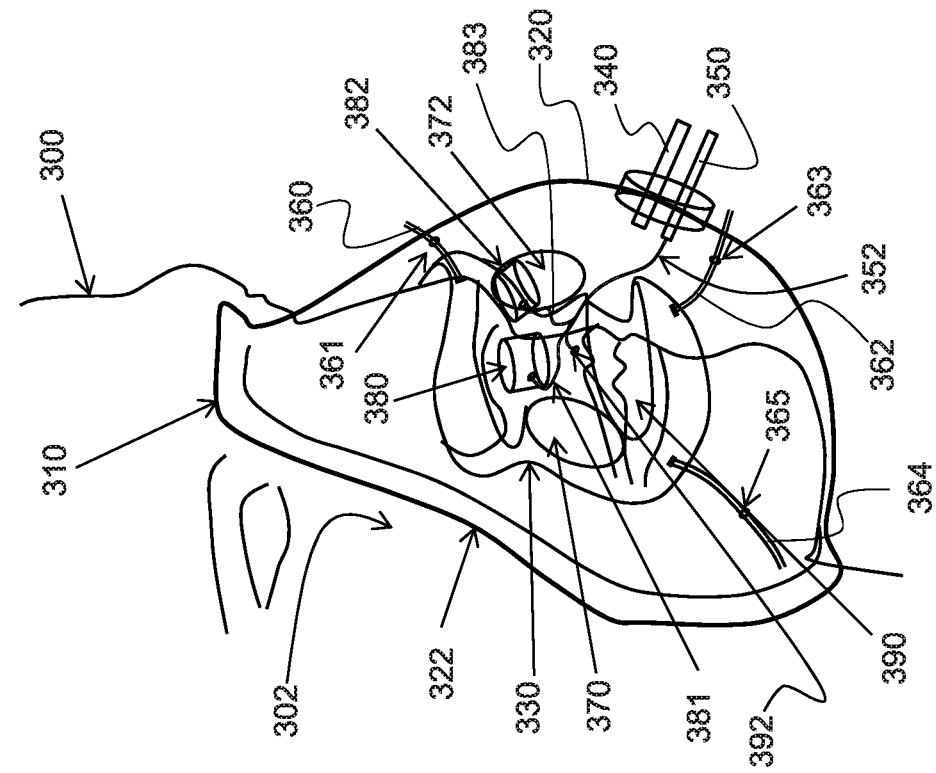

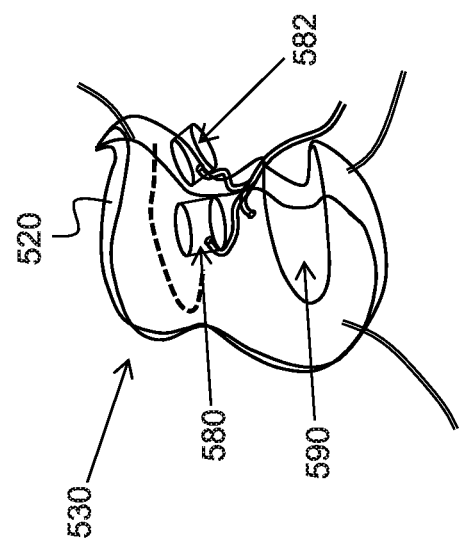
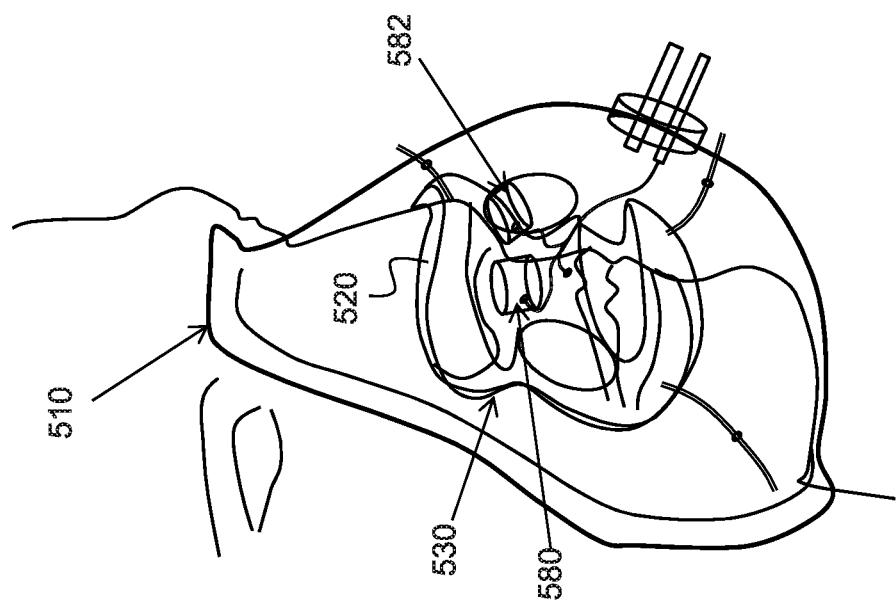
Fig. 5B
Fig. 5A

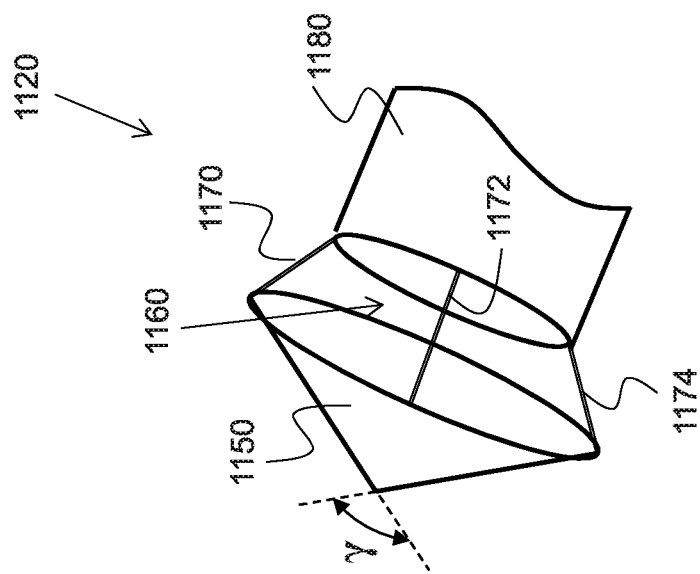
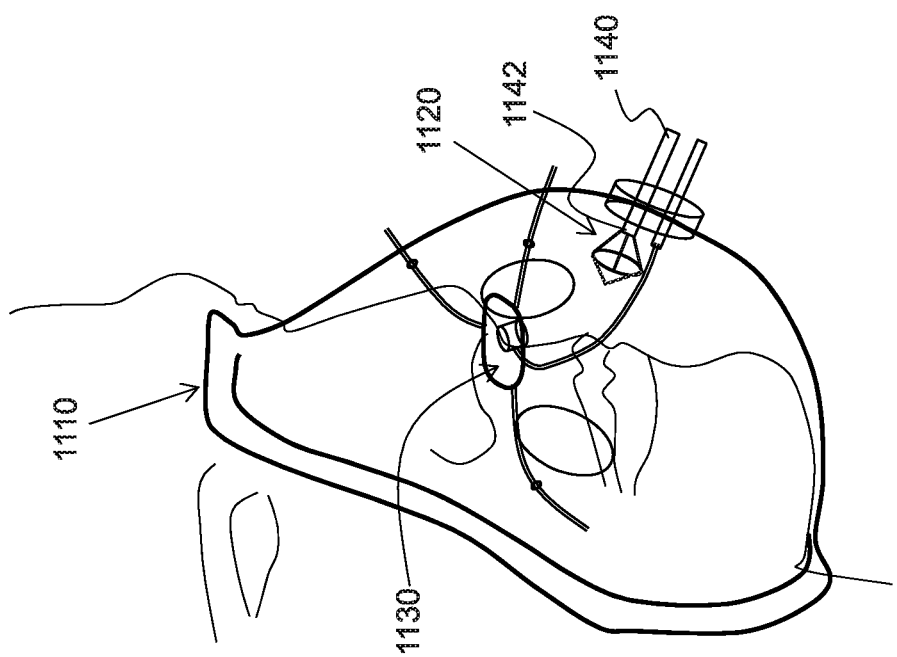
Fig. 11B
Fig. 11A

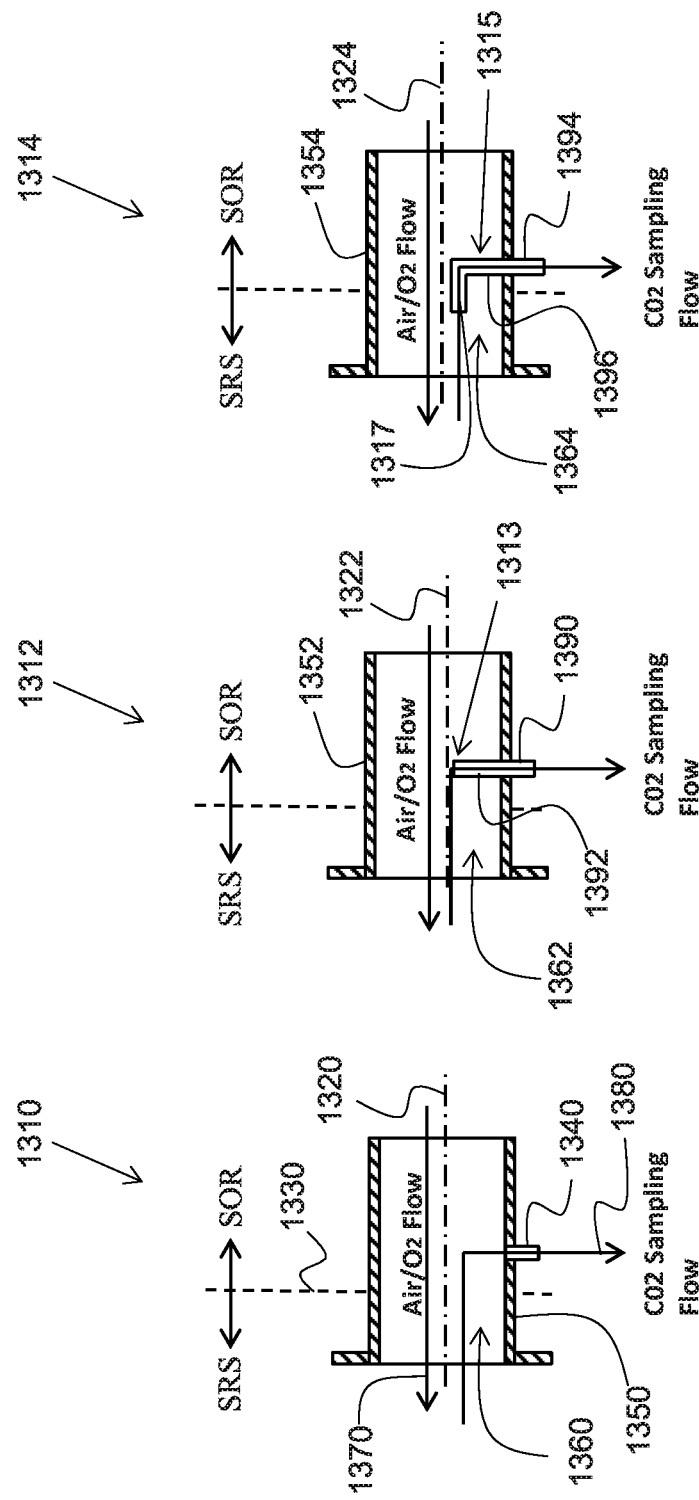

OXYGEN-CAPNOGRAPHY MASK FOR CONTINUOUS CO2 MONITORING

CROSS REFERENCE TO RELATED APPLICATIONS

This application is a Non-Provisional Application claiming priority to U.S. Provisional Patent Application No. 62/373,170, entitled "OXYGEN-CAPNOGRAPHY MASK FOR CONTINUOUS $CO_2$ MONITORING," filed Aug. 10, 2016, which is herein incorporated in its entirety for all purposes.

FIELD OF THE INVENTION

The present disclosure relates to face masks for delivering oxygen to, and monitoring gases (e.g., carbon dioxide) exhaled from, a patient and, more particularly, to a face mask that impedes dilution of an exhaled gas by a delivered gas, and vice versa.

BACKGROUND

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

A human respiratory cycle includes a sequence of events during which a human inhales and exhales a given volume of air through the respiratory system. The respiratory system includes the lungs that, during breathing, take in oxygen and expel carbon dioxide, a waste gas. An exchange of oxygen and carbon dioxide in the lungs can be evaluated, for example, by measuring oxygen saturation level in the blood and concentration of exhaled carbon dioxide. After carbon dioxide is exhaled, another respiratory cycle begins with the next breath.

Normal levels of both blood oxygen saturation and concentration of exhaled carbon dioxide can attest to the healthiness of the respiratory system. However, even if one's blood oxygen saturation level is normal, there may still be respiratory dysfunction that may be caused by the inability of body cells to use oxygen that is absorbed in the blood. In general, the higher the incompetence of body cells to exploit, the lower the level of the carbon dioxide produced by these cells and, consequently, the lower the concentration of the carbon dioxide that the subject exhales.

Face masks for subjects suffering from, prone to, or susceptible to breathing problems typically include an oxygen port for delivering oxygen to a subject at a designated rate and a carbon dioxide port for sampling exhaled carbon dioxide. Conventional masks that include the two ports have some drawbacks. One drawback is that the sampled carbon dioxide gas is diluted by the oxygen gas flow, which has to be delivered to the subject continuously. Diluting the carbon dioxide gas by the oxygen (or by any other gas for that matter) decreases. Another drawback of conventional face masks is that the carbon dioxide sampling port is distant from the subject's nose and mouth, which may also detrimentally affect the carbon dioxide concentration measurement due to, for example, the flow dispersion pattern of the exhaled $CO_2$. Another drawback of conventional face masks is that the carbon dioxide sampling port has to stay in a same position relative to the subject's nose and mouth in order to have a reliable $CO_2$ concentration measurement. However, the carbon dioxide sampling port in conventional face masks is prone to movement due to movement of the subject's head. In addition, positioning a $CO_2$ sampling port within a stagnation space within the oxygen mask causes a rebreathing effect where, in some breathing regimens, the concentration level of the $CO_2$ near, or at, the sampling port may deviate from the actual end-tidal values. (In a capnogram, which is a $CO_2$ waveform displayed by a capnograph, an end-tidal $CO_2$ (EtCO2) is the partial pressure of $CO_2$ at the end of an exhaled breath.). These drawbacks (to name a few) can result in an inaccurate measurement of the concentration of exhaled carbon dioxide. FIG. 1 illustrates an example of a face mask 100 for monitoring exhaled $CO_2$ while administering oxygen. Face mask 100 typically includes latex-free soft medical grade resin 110 that makes the mask comfortable for subjects to wear. Mask 100 includes a face side 120 and a 'tubing' side 130. Tubing side 130 includes an oxygen delivering port 140 via which oxygen can be administered to the mask wearer, and a $CO_2$ sampling port 150 via which $CO_2$ exhaled by the mask wearer can be monitored.

Carbon dioxide sampling port 150 has a longitudinal axis 152. Patient's nose 160 has a longitudinal nostril axis 162. $CO_2$ sampling port 150 (and also the adjacent oxygen port 140) is at an acute angle 170 relative to longitudinal nostril axis 162 such that $CO_2$ sampling port 150 and oxygen port 140 are placed between the nose (160) and mouth 170 of the patient. In such mask configuration neither $CO_2$ sampling port 150 nor oxygen port 140 is clearly aligned with any of nose 160 or mouth 170. Indiscriminately placing $CO_2$ sampling port 150 and oxygen port 140 in the way shown in FIG. 1 results in the drawbacks described above.

A slightly better solution is shown in FIG. 2, which shows a face mask similar to a face mask that is manufactured by MERCURY MEDICAL, a U.S. company manufacturing airway management devices. Referring to FIG. 2, mask 200 includes a 'sit', or 'knee', 210 that is oriented (220) approximately at a right angle relative to nostril orientation 230 of nose 240. Mounting oxygen delivering port 250 and $CO_2$ sampling port 260 on sit/knee 210 of mask 200 better aligns them with nostril orientation 230. ($CO_2$ sampling port 260 has an alignment 270 that forms an acute angle 280 with nostril orientation 230 that is smaller than acute angle 170 in FIG. 1.) However, mask 200 does not really solve the problems described above since mask 200 has issues similar to those related to mask 100 because $CO_2$ sampling port 260 is distant from the patient's mouth and nose. Therefore, at least in terms of exhaling carbon dioxide, neither of mask 100 and mask 200 is preferable over the other.

It would be beneficial to have a face mask that minimizes mutual interference between the two functions—delivering of oxygen to a subject and sampling of $CO_2$ exhaled by the subject. It would also be beneficial to have a face mask that is capable of measuring concentration of $CO_2$ with the same efficiency and accuracy independently of whether the subject breathes through his nose, mouth, or both.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

A face mask for delivering oxygen to, and sampling carbon dioxide exhaled from, a subject includes an internal partition wall ("IPW") that divides the mask into a subject respiratory space ("SRS") that primarily contains carbon dioxide exhaled by the subject, and a subject oxygen reservoir ("SOR") space that primarily contains oxygen. The partition wall includes one or two holes to which naris conduits are respectively connected. The naris conduit(s) is(are) positioned in proximity to the subject's nares to closely obtain carbon dioxide samples. The naris conduits are configured such that they enable oxygen to flow from the SOR space to the SRS during inhalation while quickly expelling traces of $CO_2$, and such that exhaled $CO_2$ quickly fills up the naris conduits during exhalation while expelling oxygen traces back to the SOR. Thus, forming a SRS in the mask prevents dilution of $CO_2$ during exhalation and, therefore, results in a more accurate measurement of $CO_2$ concentration.

BRIEF DESCRIPTION OF THE DRAWINGS

Various embodiments are illustrated by way of example in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures:

FIG. 3A illustrates an oxygen/capnography mask with an internal partition wall according to an example embodiment;

FIG. 3B shows the internal partition wall of FIG. 3A;

FIG. 3C shows a naris conduit according to an example embodiment;

FIG. 5A illustrates an oxygen/capnography mask with an internal partition wall that is laid over the patient's face according to another example embodiment;

FIG. 5B shows the internal partition wall of FIG. 5A;

FIG. 11A illustrates an oxygen/capnography mask with an oxygen dispenser according to another example embodiment;

FIG. 11B shows the oxygen dispenser of FIG. 11A;

FIG. 13A illustrates a naris conduit with a $CO_2$ sampling port according to example embodiments;

FIG. 13B illustrates a naris conduit with a $CO_2$ sampling port according to example embodiments; and FIG. 13C illustrates a naris conduit with a $CO_2$ sampling port according to example embodiments.

DETAILED DESCRIPTION OF THE INVENTION

Figure 2:
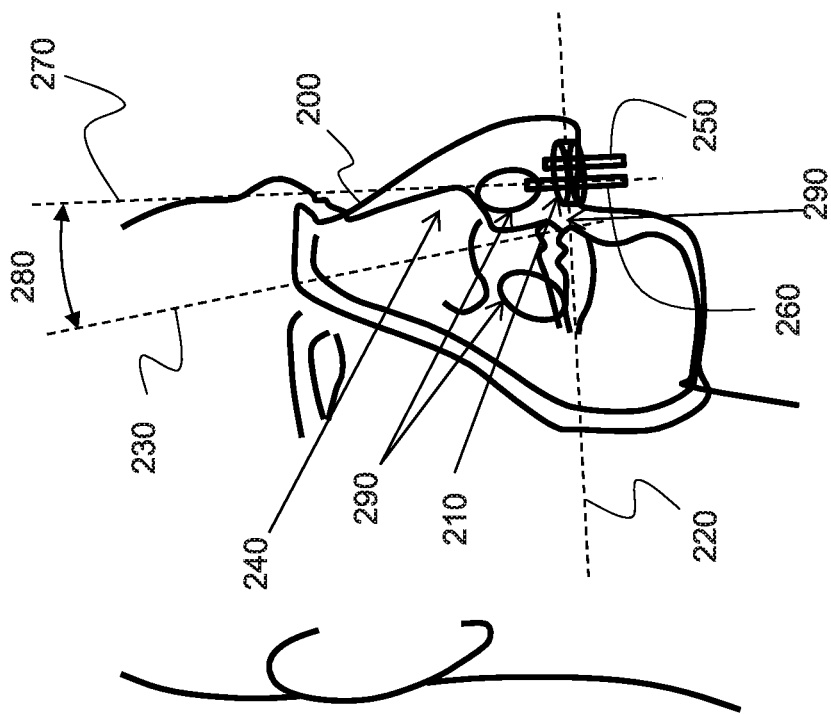
FIG. 2 (prior art) illustrates an oxygen/capnography mask which is a variant of the oxygen mask of FIG. 1.
Figure 1:
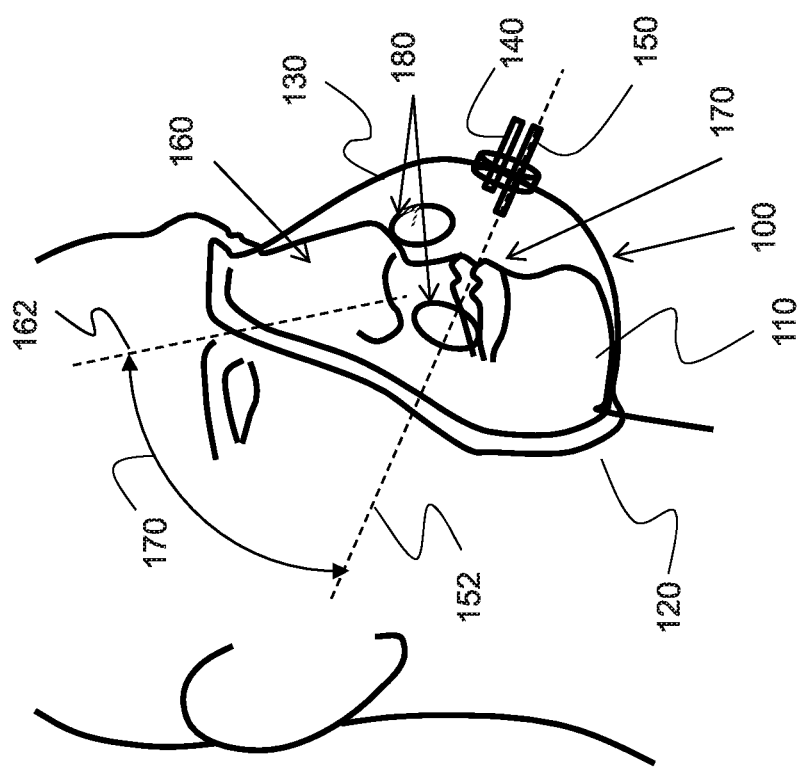
FIG. 1 (prior art) shows an oxygen mask provided with a $CO_2$ sampling port.

One or more specific embodiments of the present disclosure will be described below. These described embodiments are only examples of the presently disclosed techniques. Additionally, in an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but may nevertheless be a routine undertaking of design, fabrication, and manufacture for those of ordinary skill having the benefit of this disclosure.

The oxygen mask subject of the present disclosure includes a partition wall for operationally separate between the oxygen delivering function on the one hand, and the carbon dioxide sampling function on the other hand. as described in detail below, mask has a mask internal space and is configured to be laid over a face of a subject. The mask has an internal partition wall that is positioned inside the mask and defines, in the mask internal space, a subject respiration space (SRS) and a subject oxygen reservoir (SOR). In some embodiments, the internal partition wall may generally include a first naris conduit that extends from the inner partition wall into the SRS and into the SOR, and provides, through the internal partition wall, a bi-directional fluid flow channel between the SRS and the SOR. (When the mask is laid over the face of a subject, the first naris conduit is configured to be positioned in close proximity to the subject nares.) The internal partition wall may also include a first carbon dioxide conduit whose distal end is connected to the first naris conduit and is in fluid flow communication with an interior space of the first naris conduit. In other embodiments, the internal partition wall may also include a second naris conduit that extends from the inner partition wall into the SRS and into the SOR, and provides, through the internal partition wall, a bi-directional fluid flow channel between the SRS and the SOR. (When the mask is laid over the face of a subject, the first naris conduit is configured to be positioned in close proximity to the subject nares.) The internal partition wall may also include a second carbon dioxide conduit whose distal end is connected to the second naris conduit and is in fluid flow communication with an interior space of the second naris conduit.

FIG. 3A shows a person 300 wearing a domed oxygen/capnography face mask 310 on her/his face 302 according to an example embodiment of the present invention. Mask 310 includes a dome (convex) shaped side having an apex 320 and an open side base 322 opposite to apex 320. (The mask's open side, or mask's base, 322 is designed to fit snugly onto a patient's face, using a relatively soft seal for example.) Mask 310 includes a generally flat 'oral-nasal' internal partition wall (IPW) 330. (FIG. 3B shows IPW 330 more clearly.) IPW 330, which is positioned inside the domed mask 310 and fully covers the patient's nares and mouth, internally divides mask 310 into two spaces. One main space of mask 310 is referred to herein as a subject respiration space (SRS). The SRS is a mask space or cavity defined by or between IPW 330 and the mask's base 322 (and/or with subject's face 302) when mask 310 is laid over the subject's face. The other main space of mask 310 is referred to herein as a subject oxygen reservoir (SOR). The SOR is a mask space or cavity defined by or between IPW 330 and mask's apex 320.

Mask 310 may include an oxygen port 340 to deliver oxygen to the patient, and a $CO_2$ port 350 to extract samples of the $CO_2$ exhaled by the patient. Oxygen port 340, which may be a relatively short tube (e.g., two centimeters long), may be mounted anywhere on mask 310, provided that it can fill up the subject oxygen reservoir (SOR) with oxygen, hence the term 'oxygen reservoir'. Carbon dioxide port 350 is coupled to the subject respiration space (SRS) via a $CO_2$ tube 352 and corresponding tubing manifold. Structural constraints related to the location of $CO_2$ port 350 on mask 310 may be more lenient relative to the structural constraints related to the location of oxygen port 340 because $CO_2$ port 350 is connected to the naris conduits via a tubing system (e.g., via CO2 conduits 381 and 383), so positioning of $CO_2$ port 350 is flexible, as opposed to oxygen port 340 whose positioning affects the mixing dynamics of the two gasses.

Mask 310 may also include an IPW adjustment mechanism to adjust the (and after the adjustment to maintain the adjusted) spatial location and orientation of IPW 330 in mask 310, so that, when in use, IPW 330 is operationally maintained at an optimal distance from, and in optimal orientation with respect to, the patient's face in terms of breathing and $CO_2$ monitoring efficacy. The adjustment mechanism may be connected to IPW 330 and operable via a user (e.g., physician) through holes in mask 310. By way of example, the gap adjustment mechanism may include three elongated adjustment rods or shafts 360, 362 and 364. (Other numbers of adjustment rods or shafts may be used.) Mask 310 may include three external through holes 361, 363 and 365 through which adjustment rods or shafts 360, 362 and 364 may respectively be individually and independently pushed deeper into the mask (that is, pushed forward or closer to the patient's face), or pulled back (that is, away from the patient's face). Adjustment rods or shafts 360, 362 and 364 may be set such that IPW 330 is maintained at some distance from the face of the patient so that it does not touch the face.

Through holes 361, 363 and 365 and adjustment rods/shafts 360, 362 and 364 may be configured such that the lengthwise position of each adjustment rod or shaft in the respective through hole in mask 310 is maintained by a static friction force that exists between the rod or shaft and the hole. The friction force may, nevertheless, enable a user (e.g., physician) to adjust the lengthwise position of each rod or shaft by pushing the rod or shaft into the mask or pulling it back by applying a force that is large enough to overcome the static friction. Mask 310 may also include two pressure relief openings 370 and 372 that enable exhaled air with high $CO_2$ concentration flow to flow out of the mask due to slight overpressure that is produced by continues oxygen inflow, to thus prevent building up of excessive pressure inside the mask and rebreathing phenomena when a patient rebreathes part of a previously exhaled air with high $CO_2$ concentration. Of course, any other suitable adjustment mechanism may be used.

One naris conduit 380, or two naris conduits 380 and 382, may be mounted to, or through, IPW 330 and positioned in close proximity to the subject's nares when the mask is laid over the face of the subject. A naris conduit (e.g., naris conduit 380) may extend from IPW 330 into the SRS and into the SOR, to provide, through IPW 330, a bi-directional fluid flow channel between the SRS and the SOR.

Referring to FIG. 3B, IPW 330 may include (e.g., by forming therein) three breathing openings: two 'nares' breathing openings ("NBOs") that are positioned in close proximity to the patient's nares 384, and a mouth breathing opening ("MBO") 390 that is positioned in close proximity to the patient's mouth, when mask 310 is laid over the face of a subject. Two naris conduits (e.g., tubes) 380 and 382 are respectively mounted to the two NBOs. Each of naris conduits 380 and 382 passes through a respective opening in IPW 330 and extends outwardly from IPW 330 into the subject respiration space (SRS) and also into the subject oxygen reservoir (SOR), thus providing a bi-directional fluid flow channel between the SRS and the SOR, as described herein. Naris conduits 380 and 382 are 'breathing conduits' because they are used for both delivering oxygen to the patient and releasing (for extracting samples of) the $CO_2$ that the patient exhales. The way naris conduits 380 and 382 function is described in more detail below, for example in connection with FIG. 3C. MBO 390 provides a passage between the SOR and the SRS, so that oxygen may freely pass from the SOR to the SRS. During exhalation through the mouth, a $CO_2$ conduit 392 may be used to extract $CO_2$ samples. Carbon dioxide conduit 392, which may be positioned in a region near the mouth, is in fluid flow communication with the SRS.

A $CO_2$ extraction tubing system ("ETS") is attached to IPW 330 in order to monitor $CO_2$ that is exhaled from the patient's nares and mouth. Depending on the number of naris conduits that the IPW includes (one naris conduit; e.g., naris conduit 380, or two naris conduits; e.g., naris conduits 380 and 382), the $CO_2$ ETS may respectively include a first $CO_2$ conduit (e.g., $CO_2$ conduit 381) and a second $CO_2$ conduit (e.g., $CO_2$ conduit 383). A distal end of each $CO_2$ conduit is connected to a respective naris conduit such that it is in fluid flow communication with an interior space of that naris conduit. The distal end of the first $CO_2$ conduit (e.g., $CO_2$ conduit 381) may be positioned in close proximity to a first naris (one of patient's nares 384, FIG. 3B), and the distal end of the second $CO_2$ conduit (e.g., $CO_2$ conduit 383) may be positioned in close proximity to a second naris (the other naris of nares 384). In some other embodiments, the $CO_2$ ETS may also include $CO_2$ conduit 392 that has a distal end that is positioned in proximity to the patient's mouth (and in fluid flow communication with the SRS.) Each of $CO_2$ conduits 381, 382 and 392 has a proximal end that may be connected to a common $CO_2$ conduit 352 via a tubing manifold. (Carbon dioxide conduit 381, $CO_2$ conduit 383 and $CO_2$ conduit 392 may be connected to the $CO_2$ port 350 via common conduit 352).

During use of mask 310, oxygen is constantly provided to mask 310 via oxygen port 340, and oxygen constantly fills up the SOR space inside mask 310, ready to be inhaled by the patient. During inhalation, oxygen is delivered to the patient through naris conduits 380 and 382, and also through mouth breathing opening (MBO) 390. Most of the oxygen that is contained in mask 310 is contained in the oxygen reservoir part of the mask (in the SOR space), and it is readily available for the patient during inhalation. When the patient exhales $CO_2$ ($CO_2$ enriched air), the exhaled $CO_2$ quickly supersedes/displaces oxygen in the SRS part of mask 310, and, in particular, the oxygen in nares conduits 380 and 382, and the oxygen adjacent to the $CO_2$ conduit 392. Since the volume of the spaces in nares conduits 380 and 382 and around the patient's mouth are relatively small (e.g., relative to an amount of oxygen and $CO_2$ exchange during one breath cycle), the exhaled $CO_2$ supersedes most, if not all, of the oxygen in these spaces quickly, thus preventing dilution of $CO_2$ and enabling a more reliable sampling of the exhaled $CO_2$, and, therefore, a more reliable measurement of the concentration level of $CO_2$.

Referring to FIG. 3C, reference numeral 330' is a symbolic representation of inner partition wall (IPW) 330 that separates between the SRS space and the SOR space. The description of naris conduit 380 also applies to naris conduit 382 (with $CO_2$ conduit 381 replaced with $CO_2$ conduit 383), as each of naris conduit 380 and naris conduit 382 is primarily intended for a different naris of the patient. 'A naris conduit primarily intended for a particular naris' means that a particular naris conduit; e.g., naris conduit 380, may deliver more oxygen to the 'intended' naris, which is the naris adjacent to that naris conduit, though some of the oxygen that pass through the particular naris conduit may reach the other naris, and, similarly, most of the $CO_2$ exhaled from a particular naris reaches the 'intended' naris conduit, which is the adjacent naris conduit, though some $CO_2$ may reach the other naris conduit.)

Naris conduit 380 is substantially perpendicular to, and extends outwardly from both sides of, IPW 330' (that is, from it extends from the 'SRS' side of IPW 330' into the SRS space, and from the 'SOR' side of IPW 330' into the SOR space), and thus naris conduit 380 provides a bi-directional fluid flow channel between the SRS and the SOR spaces. Naris conduit 380 includes a $CO_2$ extraction hole 384 to which $CO_2$ conduit 381 is fixedly mounted. The distal end of conduit 381 may be aligned with the surface of naris conduit 380 or protrude into internal space 385 of naris conduit 380, and be in fluid flow communication with internal space 385 of naris conduit 380.

Naris conduit 380 has a length L and an internal diameter D. Carbon dioxide conduit 381, which is fixedly connected to naris conduit 380, has a diameter d (d<D), as shown in FIG. 3C. The values of L and D, and the ratio R=d/D, may be optimized in terms of fluid dynamics according to expected breathing characteristics (e.g., breathing cycle, breathing efficacy, etc.) of patients, and also in terms of re-breathing effect (e.g., minimizing this effect). For example, the values of L, D and R may be set such that, during a breathing-in phase of a breathing cycle, $CO_2$ traces from the previous exhalation phase are quickly expelled (evacuated) from space 385 inside naris conduit 380 through conduit 381, and, space 385 is quickly filled up with oxygen so that oxygen (or oxygen-enriched air) is readily available to the patient during inhalation. In addition, the values of L, D and R may be set such that, during a breathing-out phase of the breathing cycle, the $CO_2$ exhalation dynamics (e.g., $CO_2$ pressure and flow rate) can quickly clear space 385 from oxygen (e.g., by expelling the oxygen from naris conduit 380 back into the SOR) and fill up space 385 with $CO_2$. (By 'quickly' is meant before the relevant breathing phase ends.) The effect of the optimization of the values of L, D and R is that during inhalation, the patient inhales only, or mostly, oxygen or oxygen-enriched air, and during exhalation the $CO_2$ sampling system receives $CO_2$ with genuine concentration level. In other words, the better the optimization of the values of L, D and R, the lesser the amount of oxygen that dilutes $CO_2$ samples during exhalation, and the lesser the amount of $CO_2$ in the inhaled oxygen. (When the values of L, D and R are optimized, the amount of oxygen diluting the $CO_2$ sample is negligible.)

During inhalation of oxygen, the subject, by breathing in, creates a sub-atmospheric pressure that draws from the oxygen reservoir (SOR) into the patient's respiratory space (SRS), and ultimately into the subject's lungs, only the amount of oxygen that is required for breathing, while the remainder of the oxygen contained in the SOR is held in reserve (and partially flows out of mask 310 through pressure relief openings 370 and 372), ready for use during subsequent inhalations.

By creating two, separate, spaces by partition wall 330—one space which is the subject respiratory space, and another space which primarily contains oxygen—and manipulating the exchange of oxygen and $CO_2$ in the nares conduits 380 and 382, and near mouth opening 390, the oxygen inhaled by a patient is not diluted, or only negligibly diluted, by the exhaled $CO_2$, and the $CO_2$ exhaled by the patient is not diluted, or only negligibly diluted, by oxygen at least in those ('interference-free') spaces from which $CO_2$ conduit 381, 383 and 392 extract $CO_2$. Because partition wall 330 is large enough to cover the subject's airways (nose and mouth) and $CO_2$ is sampled directly from the subject's airways, the concentration level of the $CO_2$ exhaled from the subject's airways (and passes through $CO_2$ conduit 381, 383 and 392, and finally through $CO_2$ sampling port 350) remains substantially the same even when the mask slightly moves on the subject's face. In addition, since the $CO_2$ conduit 381, 383 and 392 cover the subject's two nostrils and mouth, and partition wall 330 is large, partition wall 330 averages the $CO_2$ exhaled by the various patient's airways. Therefore, an issue that may exist in other types of oxygen masks, regarding whether a patient breathes only through the nose (through one naris or through both nares) or only through the mouth, is non-existent in mask 310 or in its variants.

Figure 4B:
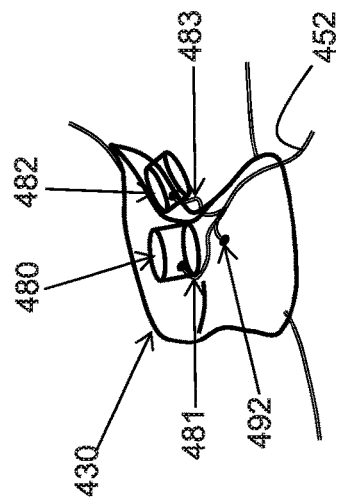
FIG. 4B shows the internal partition wall of FIG. 4A.
Figure 4C:
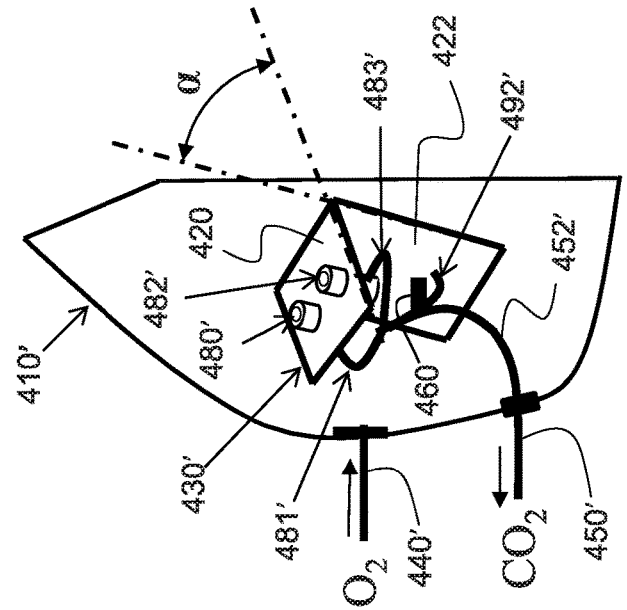
FIG. 4C illustrates a side-view of mask of FIG. 4A.
Figure 4A:
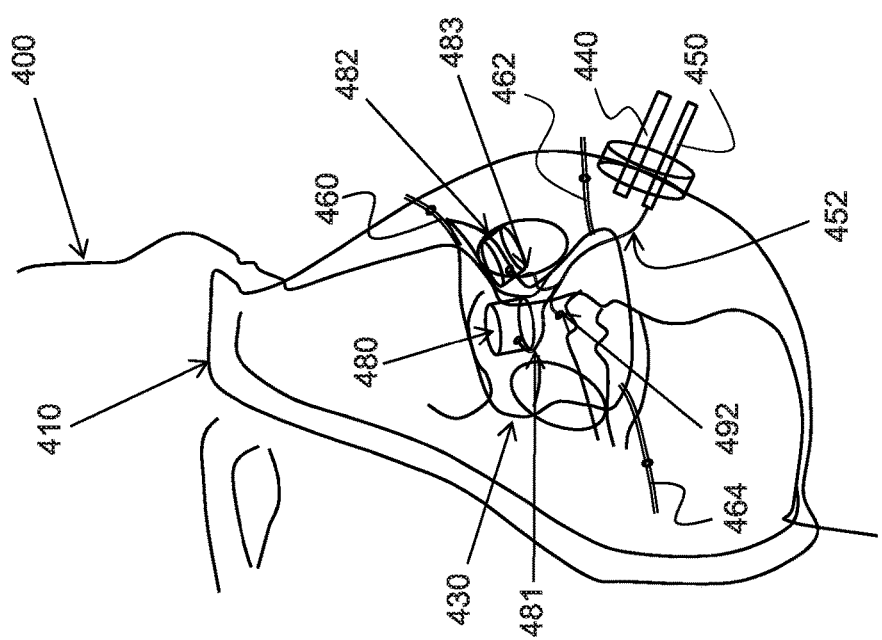
FIG. 4A shows an oxygen/capnography mask with small internal partition wall according to another example embodiment.

FIG. 4A shows an oxygen/capnography mask 410 with an internal partition wall (IPW) 430 worn on a subject 400 according to another example embodiment of the present invention. IPW 430, which is positioned inside the domed mask, is smaller than IPW 330 of FIGS. 3A-3B and is positioned in proximity to the patient's nares. (While IPW 330 fully covers the patient's nares and mouth (and, therefore, IPW 330 includes an extra breathing opening 390 for the patient's mouth, IPW 430 does not include a mouth breathing opening.) IPW 430 is kept at distance from the patient's face by using an adjustment mechanism that includes, in this example, adjustment rod or shaft 460, 462 and 466. In this embodiment, IPW 430 is smaller than IPW 330 and partly covers the nares and mouth of the patient.

IPW 430 includes two naris breathing openings to which two naris conduits 480 and 482 are respectively connected in a similar way as shown in FIGS. 3A-3B. To naris conduits 480 and 482 are respectively connected $CO_2$ conduit 481 and $CO_2$ conduit 483 that function and are optimized in a similar way as $CO_2$ conduit 381 and $CO_2$ conduit 383 of FIGS. 3A-3C.

A carbon dioxide conduit 492 is positioned near, or in close proximity to, the patient's mouth and functions in a similar way as CO$_2$ conduit 392 of FIGS. 3A-3B. CO$_2$ conduits 481 and 482 are positioned adjacent, or in close proximity, to the patient's nares and function in a similar way as CO$_2$ conduits 381 and 382 of FIGS. 3A-3B. Carbon dioxide conduits 481, 482 and 492 have a proximal end, and the proximal ends of the three conduits may be connected to a common CO$_2$ conduit 452 via a tubing manifold. Mask 410 may also include: (1) an oxygen port 440 to deliver oxygen to the subject oxygen reservoir (SOR) space inside oxygen/capnography mask 410, and (2) a CO$_2$ sampling port 450 that is connected to CO$_2$ conduit 452 through which exhaled carbon dioxide may be extracted by a CO$_2$ sampling system. (FIG. 4B shows IPW 430 and its tubing system more clearly.)

FIG. 4C shows a schematic view of mask 410 of FIG. 4A. Mask 410' includes a flat IPW 430' that is roughly or approximately "L" shaped. One 'leg' (leg 420) of L-shaped IPW 430' is positioned in proximity to the patient's nares, so it includes two naris conduits (naris conduits 480' and 482') to which CO$_2$ conduits 481 and 483 are respectively connected in order to obtain therefrom CO$_2$ samples from the CO$_2$ that is exhaled from the patient's nose. The other leg (leg 422) of L-shaped IPW 430' is positioned in proximity to the patient's mouth, so it includes a through hole to which CO$_2$ conduit 492 is connected in order to obtain CO$_2$ samples exhaled from the patient's mouth. IPW 430 (and IPW 430') has similar benefits as IPW 330 and is subjected to similar optimization it terms of dimensions. An angle α between the legs 420 and 422 of IPW 430' may be subjected to optimization in terms of separation between oxygen and CO$_2$ during breathing. An elongated conduit fixation member 460 may be connected to IPW 430' (e.g., to leg 422), on the one hand, and to conduit 452', on the other hand, and keep the CCO$_2$ 2 tubing, as a whole, in place inside the mask. Also shown in FIG. 4C are oxygen port 440', CO$_2$ port 450' and a CO$_2$ conduit that collects CO$_2$ samples from CO$_2$ conduits 481', 483' and 492'.

FIG. 5A shows an oxygen/capnography mask 510 with an internal partition wall (IPW) 530 worn on a subject 500 according to another example embodiment. IPW 530, which is positioned inside the domed mask, is similar to IPW 330 in the sense that it also includes two includes two naris conduits 580 and 582 and a mouth breathing opening. IPW 530 differs from IPW 330 in that IPW 530 is somewhat larger than IPW 330 and includes a perimeter 520 that is adapted to tightly fit onto, and touch, the face of the patient. IPW 530 may be regarded as a small mask inside mask 510. FIG. 5B shows IPW 530 and the CO$_2$ tubing more clearly. IPW 530 is larger than IPW 330 and covers the nose tip and the mouth of the patent.

Figure 6B:
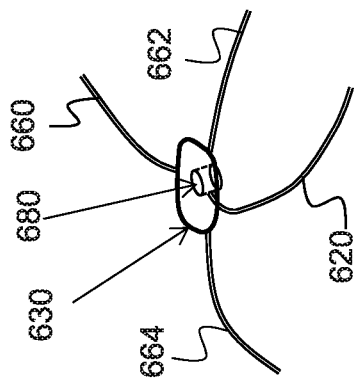
FIG. 6B shows the internal partition wall of FIG. 6A.
Figure 6A:
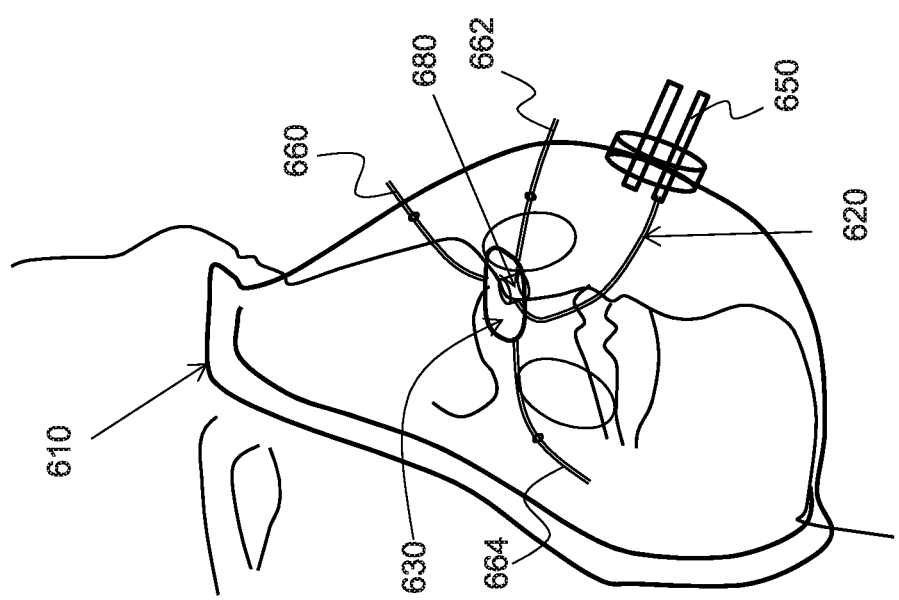
FIG. 6A illustrates an oxygen/capnography mask with an internal partition wall according to yet another example embodiment.

FIG. 6A shows an oxygen/capnography mask 610 with an internal partition wall (IPW) 630 according to another example embodiment. IPW 630 is very small relative to IPWs 330, 430 and 530, and is positioned near the nares of the patient. IPW 630, which is positioned inside the domed mask, has a size that complies with the width of the nares; that is, IPW 630 may have a size that is similar to (e.g., somewhat smaller than, or somewhat larger than) the width of the subject's nose. (The size of an IPW can be reduced to any size that still imparts it the functionalities and benefits described herein.) IPW 630 may be shaped like a scoop in order to more efficiently capture CO$_2$ from the patient's nares in a region where the CO$_2$ cannot be washed away by oxygen. (The patient may breathe normally via the mouth without affecting, or be effected by, the breathing and CO$_2$ monitoring via IPW 630.) By way of example, IPW 630 includes at least one naris conduit, which is shown at 680.

(Naris conduit 680 is similar to, and functions in a similar way as, naris conduits 380, 480 and 580. Naris conduit 680 may also be subjected to a similar optimization calculation.) IPW 630 may be positioned in a region between the patient's upper lip and nose, and naris conduit 680 may be centered between the two nares in order to capture CO$_2$ that is exhaled from both nares. A CO$_2$ conduit 620 is connected between a through hole in naris conduit 680 and a CO$_2$ port 650 so that CO$_2$ can be extracted from naris conduit 680 and delivered to a CO$_2$ monitoring system via CO$_2$ port 650. IPW 630 is kept at distance from the patient's face by using an adjustment mechanism that includes, in this example, adjustment rod or shaft 660, 662 and 666. (FIG. 6B shows IPW 630 more clearly.)

IPW 630 may be made of a flat thin plastic material whose surface has an area that is small but large enough to produce, during exhalation, a dynamic CO$_2$ pressure that is high enough to expel oxygen from the region between the patient's nose and mouth, leaving there only, or mostly, CO$_2$ from which CO$_2$ samples can be extracted through CO$_2$ conduit 620.

Figure 7B:
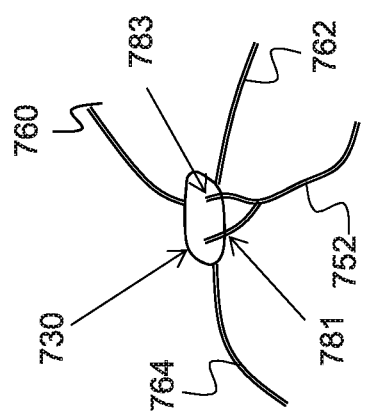
FIG. 7B shows the internal partition wall of FIG. 7A.
Figure 7A:
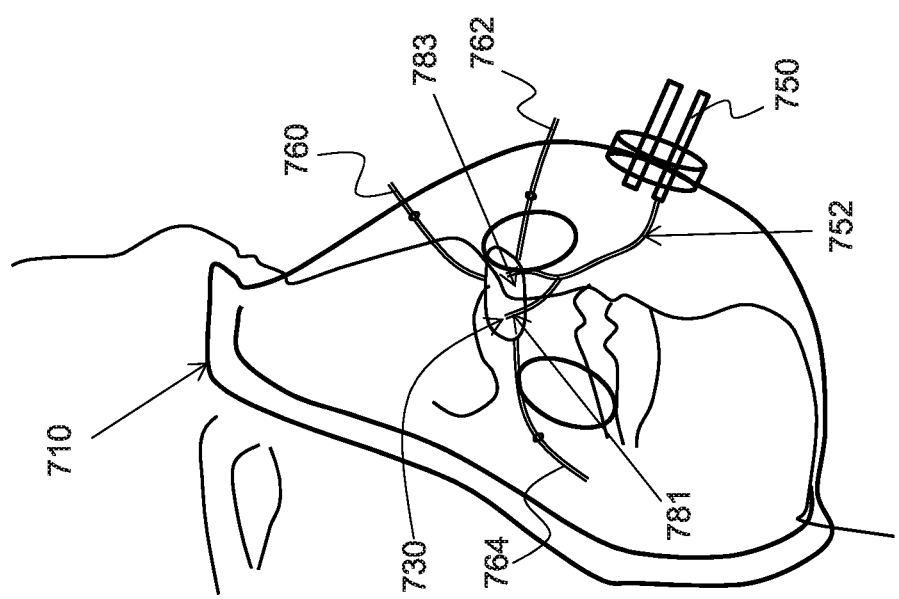
FIG. 7A illustrates an oxygen/capnography mask with an internal partition wall according to still another example embodiment.

FIG. 7A shows an oxygen/capnography mask 710 with an internal partition wall (IPW) 730 according to another example embodiment. IPW 730, which is positioned inside the domed mask, is similar to IPW 630 in terms of size. (IPW 730 is also very small relative to IPWs 330, 430 and 530, and is positioned near the nares of the patient.) IPW 730 differs from IPW 630 in that IPW 730 does not include naris conduits. Instead, two CO$_2$ conduits 781 and 783 are connected to CO$_2$ extracting openings in IPW 730 and function in a similar way as CO$_2$ conduits 381 and 383 of FIGS. 3A-3C.

IPW 730 may be shaped like a scoop in order to more efficiently capture CO$_2$ from the patient's nares in a region where the CO$_2$ cannot be washed away by oxygen. (The patient may breathe normally via the mouth without affecting, or be effected by, the breathing and CO$_2$ monitoring via IPW 730.) IPW 730 may be positioned in a region between the patient's upper lip and nose, and the openings in IPW 730, to which the distal ends of CO$_2$ conduits 781 and 783 are connected, may respectively be positioned in front of the two nares in order to capture CO$_2$ that is exhaled from them. The proximal ends of CO$_2$ conduits 781 and 783 may be connected to a CO$_2$ conduit 752 whose other end is connected to a CO$_2$ port 750 so that CO$_2$ can be extracted from IPW 730 and delivered to a CO$_2$ monitoring system via CO$_2$ port 750. IPW 730 is kept at distance from the patient's face by using an adjustment mechanism that includes, in this example, adjustment rod or shaft 760, 762 and 766. (FIG. 7B shows IPW 730 more clearly.)

IPW 730 may be made of a flat thin plastic material whose surface has an area that is small but large enough to produce, during exhalation, a dynamic CO$_2$ pressure that is high enough to expel oxygen from the region between the patient's nose and mouth, leaving there only, or mostly, CO$_2$ from which CO$_2$ samples can be extracted through CO$_2$ conduit 752.

Figure 8:
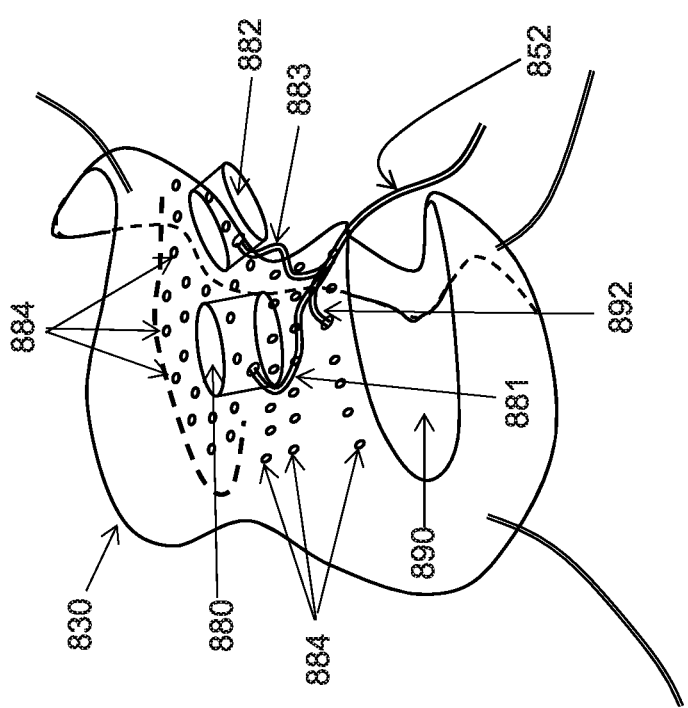
FIG. 8 shows a perforated internal partition with naris conduits according to an example embodiment.

FIG. 8 shows an inner partition wall (IPW) 830 according to another example embodiment. IPW 830 is similar to IPW 330 with the exception that IPW 830 is perforated, with the perforation slits or holes shown at 884. IPW 330 includes two naris conduits (880 and 882), a mouth breathing opening 890, and CO$_2$ tubing that includes three CO$_2$ conduits (881, 883 and 892) that are connected to a common CO$_2$ conduit 852.

IPW 830 differs from IPW 330 in that it contains perforation slits or holes. (Some of the perforation slits or holes are shown at 884, though all of the perforation slits or holes in IPW 830 are referenced by reference numeral 884.) Using perforation slits or holes such as, or similar to, perforation slits or holes 884, is beneficial because such perforation may prevent under-pressure condition in the subject respiration space (SRS) during inhalation and over-pressure condition in the SRS during exhalation, and thus facilitates breathing when a patient has breathing difficulties such as breathing in oxygen. Perforation slits or holes 884 also reduce the re-breathing effect, which is a breathing condition in which the patient breathes in $CO_2$ that is not timely washed away (from the SRS part of the mask) before inhaling oxygen. The size and arrangement (e.g., location, density) of perforation slits or holes 884 may be manipulated in order to optimize IPW 830 in terms of, for example, ease of breathing, re-breathing effect, and $CO_2$ sampling efficacy. For example, the closer the perforation slits or holes to a $CO_2$ 'sampling point' (e.g., naris conduit 880 or 882) in the IPW, the denser the perforation slits/holes. In another example, the closer the perforation slits or holes to the $CO_2$ sampling point in the IPW, the smaller the slits/holes (e.g., the smaller their diameter). By way of example, perforation slits or holes 884 are evenly distributed in IPW 830, and all slits/holes have a similar size.

Figure 9:
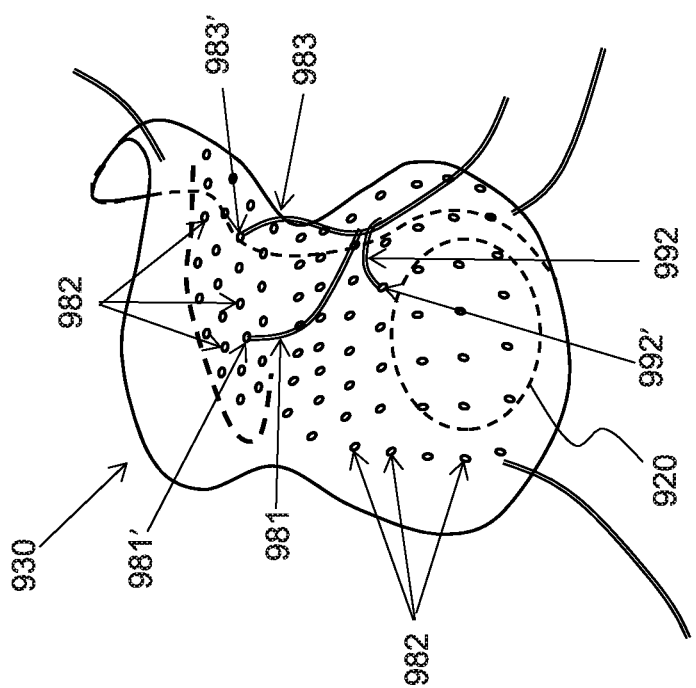
FIG. 9 shows a perforated internal partition without naris conduits according to another example embodiment.

FIG. 9 shows an inner partition wall (IPW) 930 according to another example embodiment. IPW 930 is similar to IPW 830 in the sense that it, too, includes three $CO_2$ conduits (conduits 981, 983 and 992) and perforation slits or holes (some of which are shown at 982, though reference numeral 982 refers to all perforation slits or holes in IPW 930). However, IPW 930 differs from IPW 830 in that IPW 930 does not include a mouth breathing opening and naris conduits. Instead, multiple perforation slits or holes, for example perforation slits or holes 920, are used instead of one large mouth breathing opening, and, in addition, $CO_2$ conduits 981, 983 and 992 are respectively directly connected to IPW 930 via $CO_2$ sampling, or access, points in IPW 930, where the $CO_2$ sampling, or access, points in the IPW may be perforation slits or holes; e.g., perforation slits or holes 981', 983' and 992'.

The size and arrangement (e.g., location, density) of the perforation slits or holes 982 may be manipulated in order to optimize functionality of IPW 930 in terms of ease of breathing, the re-breathing effect, and $CO_2$ sampling efficacy. For example, the closer the perforation slits or holes to a $CO_2$ sampling, or access, point (e.g., $CO_2$ sampling point 981'), the denser the slits/holes. In another example, the closer the slits or holes to a $CO_2$ sampling point (e.g., $CO_2$ sampling point 983'), the smaller the slits/holes (e.g., the smaller their diameter). By way of example, perforation slits or holes 982 are evenly distributed in IPW 930, and all slits/holes have a similar size. A $CO_2$ sampling point may be, for example, a naris conduit (e.g., naris conduit 880 or 882), as in FIG. 8, or, in the absence of a naris conduit, a perforation slit or hole (e.g., perforation slits or holes 981', 983', 992'), as shown in FIG. 9.

Figure 10B:
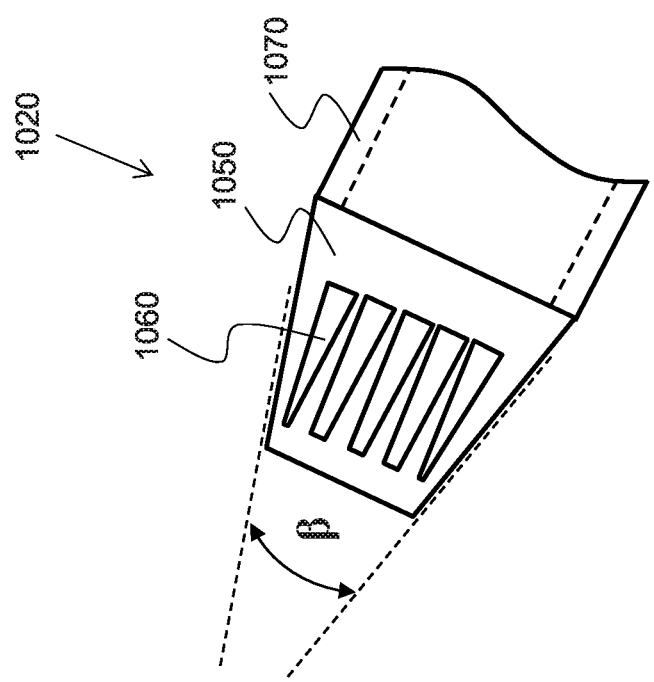
FIG. 10B shows the oxygen dispenser of FIG. 10A.
Figure 10A:
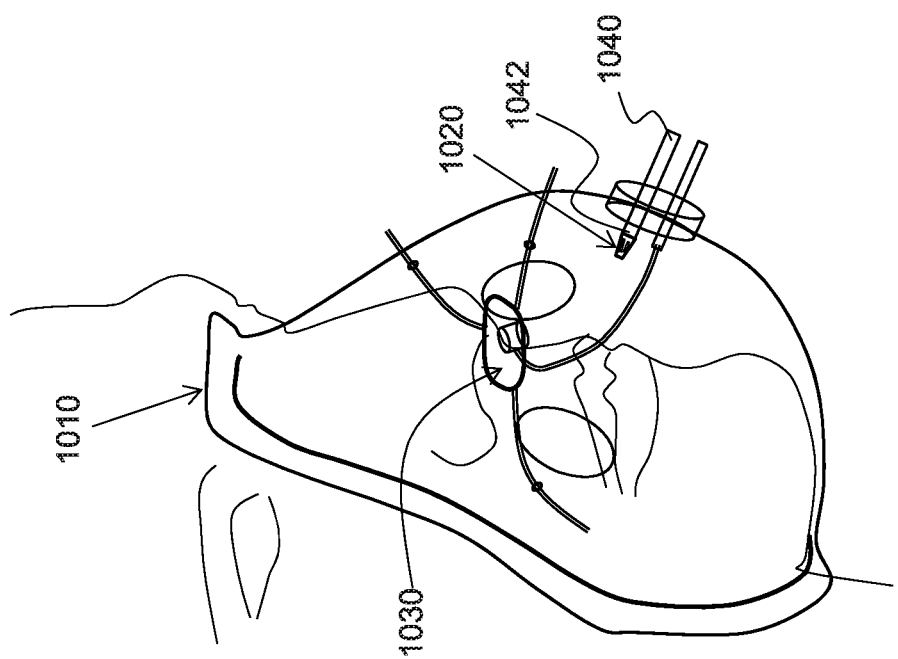
FIG. 10A illustrates an oxygen/capnography mask with an oxygen dispenser according to an example embodiment.

FIG. 10A shows an oxygen/capnography mask 1010 according to another example embodiment. Mask 1010 may include an IPW 1030 that may be similar to IPW 630. Mask 1010 includes an oxygen port 1040. Distal end 1042 of oxygen port 1040, which resides in mask 1010, may include a gas disperser 1020 (e.g., sprinkler, scatterer, sprayer, etc.) for dispersing (e.g., by spraying) oxygen into the oxygen reservoir part of mask 1010, which is most of the space inside mask 1010. Spraying oxygen into mask 1010 has a benefit over transferring it in the form of gas jet (as is the case with oxygen port 340 in FIG. 3A, for example) because an oxygen jet causes turbulences inside the mask (e.g., mask 310, FIG. 3A), and turbulences inside the mask detrimentally affect (e.g., disrupt) oxygen inhalation and $CO_2$ sampling (because turbulences mix up the two gasses). Gas disperser 1020 is shown more clearly in FIG. 10B, which is described below. Referring to FIG. 10B, gas disperser 1020 may include, at its distal end 1042, a hollow base part 1070 on top of which is mounted a hollow pointed, or tapering, member 1050 having an angle β (e.g., β=30 degrees). Pointed or tapered member 1050 may have a plurality of gas outlets, or vents, 1060 for dispersing oxygen (that is, through which oxygen can be dispersed; e.g., sprayed out) into the oxygen reservoir space of mask 1010. The gas disperser at the distal end of an oxygen port may be or include a pointed cap that is fixedly kept at distance from a hollow base. Such structure results in 'peripheral' dispersion of oxygen through an opening formed by the distance between the cap and the hollow base. FIGS. 11A-11B and 12A-12B, which are describe below, show example pointed cap like gas dispensers. (A gas disperser may include another cap or a cap similar to the cap shown in FIGS. 11A-11B and 12A-12B.)

FIG. 11A shows an oxygen/capnography mask 1110 according to another example embodiment. Mask 1110 may include an IPW 1130 that may be similar to IPW 630. Mask 1110 includes an oxygen port 1140. A distal end 1142 of oxygen port 1140, which resides in mask 1110, may include a disperser 1120 for dispersing oxygen in the oxygen reservoir part of mask 1110, which, in this embodiment, may occupy most of the space inside mask 1110. Distributing oxygen into mask 1010 in the way described below has a benefit over transferring oxygen in the form of gas jet (as is the case with oxygen port 340 in FIG. 3A, for example) because an oxygen jet causes turbulences inside the mask (e.g., mask 310, FIG. 3A), which has drawbacks as described above in connection with FIGS. 10A-10B.

Gas disperser 1120 is shown more clearly in FIG. 11B, which is described below. Referring to FIG. 11B, gas disperser 1120 may include, at its distal end 1142, a hollow base part 1180 on top of which, though distanced from base part 1180, is mounted a pointed, tapering or conical, cap 1150 having an angle γ (e.g., γ=120 degrees). Pointed cap 1150 is fixedly distanced from base part 1180 by elongated spacing members 1170, 1172 and 1174. The distance between the base of pointed cap 1150 and the base member 1180 results in a gas outlet, or vent, 1160 through which oxygen flows out into the subject oxygen reservoir (SOR) space of mask 1110 in the form of a gas 'cloud'.

Figure 12B:
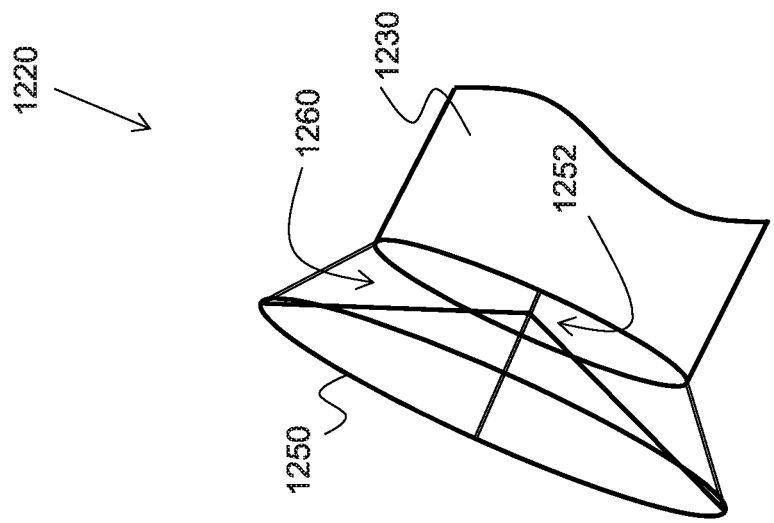
FIG. 12B shows the oxygen dispenser of FIG. 12A.
Figure 12A:
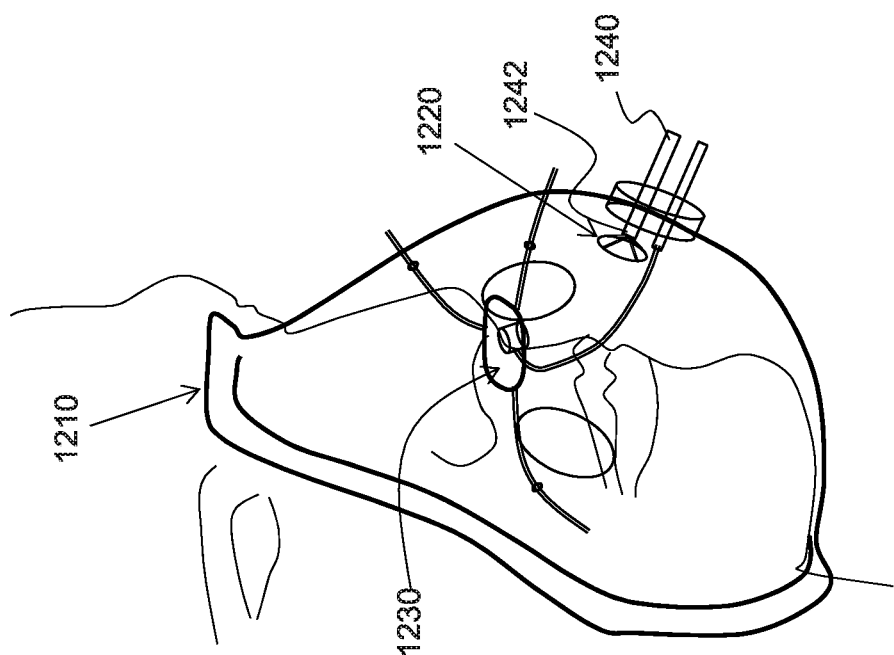
FIG. 12A illustrates an oxygen/capnography mask with an oxygen dispenser according to yet another example embodiment.

FIG. 12A shows an oxygen/capnography mask 1210 according to another example embodiment. Mask 1210 may include an IPW 1230 that may be similar to IPW 1130. Mask 1210 includes an oxygen port 1240. Distal end 1242 of oxygen port 1240, which resides in mask 1210, may include a gas disperser 1220 for distributing oxygen in the oxygen reservoir part of mask 1210, which is most of the space inside mask 1210.

Gas disperser 1220 is shown more clearly in FIG. 12B, which is described below. Referring to FIG. 12B, gas disperser 1220 may include, at its distal end 1242, a hollow base part 1230 on top of which, though distanced from base part 1230, is mounted a pointed cap 1250 that is similar to pointed cap 1150 of FIGS. 11A-11B, except that pointed cap 1250 is mounted on base part 1230 with the cap's apex 1252 turning to, or facing, the opposite direction; that is, towards base part 1230. Pointed cap 1250 is fixedly kept at distance from base part 1230 by elongated spacing members similar to those that keep pointed cap 1150 at distance from base part 1130. The distance between the base of pointed cap 1250 and the base member 1230 results in a gas outlet, or vent, 1260 through which oxygen flows out into the SOR space of mask 1210 in the form of a gas 'cloud'. FIGS. 10A-10B, 11A-11B and 12A-12B show some example gas dispersers. Alternative (e.g., other or similar) types of gas dispersers may be used.

FIGS. 13A-13C show various structures of naris conduits according to example embodiments. Referring to FIG. 13A, a naris conduit 1310 includes a longitudinal axis 1320 and is attached to or mounted on an IPW (the IPW is shown symbolically at 1330) such that IPW 1330 defines, or separates between, a subject respiration space (SRS) and a subject oxygen reservoir (SOR). Naris conduit 1310 (or its longitudinal axis 1320) may be perpendicular to IPW 1330, or it may be at an angle with respect to IPW 1330. Naris conduit 1310 also includes a $CO_2$ conduit 1340. Carbon dioxide conduit 1340 may be a short, straight, tube that is mounted on, and protrudes only outwardly from, body 1350 of naris conduit 1310. Carbon dioxide conduit 1340 may protrude from body 1350 of naris conduit 1310 perpendicularly. Carbon dioxide conduit 1340 includes an open channel that is in fluid flow communication with inner space 1360 of naris conduit 1310. During inhalation, oxygen fills up naris conduit 1310 with oxygen while oxygen is transferred (1370) through naris conduit 1310 from the SOR side to the SRS side. During exhalation, $CO_2$ exhaled by the patient forcedly expels oxygen from the interior space 1360 of naris conduit 1310 back into the SOR side, and some of the exhaled $CO_2$ (the $CO_2$ samples) are extracted (1380) through $CO_2$ conduit 1340 (and through a connecting tube) by a $CO_2$ monitoring system.

Referring to FIG. 13B, naris conduit 1312 is structurally similar to naris conduit 1310 except for the $CO_2$ conduit: the $CO_2$ conduit of (connected to) naris conduit of 1312 protrudes from body 1352 of naris conduit 1312 both outwardly (the part protruding outwardly is shown at 1390) and inwardly (into internal space 1362 of naris conduit 1312; the part protruding inwardly is shown at 1392). Distal end 1313 of the $CO_2$ conduit may reach, or be aligned with (e.g., coincide with), longitudinal axis 1322 of naris conduit 1312, or it may be shorter such that it is misaligned with longitudinal axis 1322.

Referring to FIG. 13C, naris conduit 1314 is structurally similar to naris conduits 1310 and 1312 except for the $CO_2$ conduit: like in FIG. 13B, $CO_2$ conduit 1315 of naris conduit of 1314 protrudes from body 1354 of naris conduit 1314 both outwardly, as shown at 1394, and inwardly (into internal space 1364 of naris conduit of 1314), as shown at 1396. However, $CO_2$ conduit 1315 is an "L" shaped tube having two tube sections or legs: one tube section or leg (an 'outlet' part, shown at 1394 and 1396) that is mounted on body 1354 and transfer $CO_2$ samples to a $CO_2$ monitoring system, and another tube section or leg (an 'inlet' part, shown at 1317) that is directed towards (it faces) the SRS side in order to collect $CO_2$ samples. Tube section 1317 may be parallel to (e.g., coincide with) longitudinal axis 1324 of naris conduit 1314, or it may slant with respect to longitudinal axis 1324 of naris conduit 1314.

Various aspects of the techniques disclosed herein are combinable with various types of binary-gas or multi-gas face masks. Although the discussion herein relates to face masks for delivering oxygen and sampling exhaled carbon dioxide gases, the techniques are not limited in this regard.

While certain features have been illustrated and described herein, many modifications, substitutions, changes, and equivalents will now occur to those of ordinary skill in the art, and the appended claims are intended to cover all such modifications and changes.

The invention claimed is:

1. An oxygen-capnography face mask comprising:
   a mask having a mask internal space and configured to be laid over a face of a subject;
   an inner partition wall positioned in the mask internal space and defining, in the mask internal space, a subject respiration space and a subject oxygen reservoir, the internal partition wall comprising:
   a first naris conduit, the first naris conduit extending from the inner partition wall into the subject respiration space and into the subject oxygen reservoir and providing, through the inner partition wall, a bi-directional fluid flow channel between the subject respiration space and the subject oxygen reservoir, wherein when the mask is laid over the face of a subject, the first naris conduit is configured to be positioned in close proximity to the subject nares; and
   a first carbon dioxide conduit having a distal end that is connected to the first naris conduit and is in fluid flow communication with an interior space of the first naris conduit.

2. The face mask as in claim 1, wherein the inner partition wall comprises:
   a second naris conduit, the second naris conduit extending from the inner partition wall into the subject respiration space and into the subject oxygen reservoir and providing, through the internal partition wall, a bi-directional fluid flow channel between the subject respiration space and the subject oxygen reservoir, wherein when the mask is laid over the face of a subject, the second naris conduit is configured to be positioned in close proximity to the subject nares; and
   a second carbon dioxide conduit having a distal end that is connected to the second naris conduit and is in fluid flow communication with an interior space of the second naris conduit.

3. The face mask as in claim 2, wherein, when the mask is laid over the face of the subject, the first naris conduit is positioned in proximity to one naris and the second naris conduit is positioned in proximity to the other naris.

4. The face mask as in claim 2, comprising:
   a mouth breathing opening formed in inner partition wall, the mouth breathing opening positioned in close proximity to the subject's mouth when the mask is laid over the face of the subject; and
   a third carbon dioxide conduit, the third carbon dioxide conduit having a distal end that is positioned in a region near the mouth and is in fluid flow communication with the subject respiration space.

5. The face mask as in claim 4, comprising a carbon dioxide port, wherein the first carbon dioxide conduit, the second carbon dioxide conduit and the third carbon dioxide conduit are connected to the carbon dioxide port.

6. The face mask as in claim 4, wherein the inner partition wall covers the first naris, the second naris and the mouth of the subject.

7. The face mask as in claim 4, wherein the inner partition wall partly covers the first naris, the second naris and the mouth of the subject.

8. The face mask as in claim 1, wherein the inner partition wall is "L" shaped.

9. The face mask as in claim 1, wherein the inner partition wall covers the nose tip and the mouth of the subject.

10. The face mask as in claim 1, wherein the inner partition wall has a width approximately the width of the nares.

11. The face mask as in claim 1, wherein the inner partition wall is perforated by a plurality of holes.

12. The face mask as in claim 1, wherein the first carbon dioxide conduit protrudes outwardly from the first naris conduit.

13. The face mask as in claim 1, wherein the first carbon dioxide conduit protrudes both outwardly from and inwardly into the first naris conduit.

14. The face mask as in claim 13, wherein the first carbon dioxide conduit protruding inwardly into the first naris conduit comprises a tube leg that is perpendicular to a longitudinal axis of the first naris conduit, and a tube leg that is parallel to, or coincides with, the longitudinal axis of the first naris conduit.

15. The face mask as in claim 1, comprising:
an oxygen port, said oxygen port having a distal end residing in the face mask; and
a gas disperser mounted on the distal end of the oxygen port, to disperse oxygen into the subject oxygen reservoir.

16. The face mask as in claim 15, wherein the gas disperser comprises:
a tapered member comprising a plurality of gas outlets for dispersing oxygen.

17. The face mask as in claim 15, wherein the gas disperser comprises:
a hollow base; and
a cap, the cap being fixedly kept at distance from the hollow base.

18. An oxygen-capnography face mask comprising:
a mask having a mask internal space and configured to be laid over a face of a subject;
an inner partition wall positioned in the mask internal space and defining, in the mask internal space, a subject respiration space and a subject oxygen reservoir, wherein the inner partition wall is perforated by a plurality of holes and wherein the size and arrangement of the perforation holes are optimized in terms of ease of breathing, re-breathing effect, and carbon dioxide sampling efficacy, the inner partition wall comprising:
a first naris conduit, the first naris conduit extending from the inner partition wall into the subject respiration space and into the subject oxygen reservoir and providing, through the inner partition wall, a bi-directional fluid flow channel between the subject respiration space and the subject oxygen reservoir, wherein when the mask is laid over the face of a subject, the first naris conduit is configured to be positioned in close proximity to the subject nares, and
a first carbon dioxide conduit having a distal end that is connected to the first naris conduit and is in fluid flow communication with an interior space of the first naris conduit.

19. An oxygen-capnography face mask comprising:
a mask having a mask internal space and configured to be laid over a face of a subject;
an inner partition wall positioned in the mask internal space and defining, in the mask internal space, a subject respiration space and a subject oxygen reservoir, wherein the inner partition wall is perforated by a plurality of holes, the inner partition wall comprising:
a first naris conduit, the first naris conduit extending from the inner partition wall into the subject respiration space and into the subject oxygen reservoir and providing, through the inner partition wall, a bi-directional fluid flow channel between the subject respiration space and the subject oxygen reservoir, wherein when the mask is laid over the face of a subject, the first naris conduit is configured to be positioned in close proximity to the subject nares and wherein the closer the holes to the first naris conduit or to the second naris conduit, the denser the holes; and
a first carbon dioxide conduit having a distal end that is connected to the first naris conduit and is in fluid flow communication with an interior space of the first naris conduit.

20. An oxygen-capnography face mask comprising:
a mask having a mask internal space and configured to be laid over a face of a subject;
an inner partition wall positioned in the mask internal space and defining, in the mask internal space, a subject respiration space and a subject oxygen reservoir, wherein the inner partition wall is perforated by a plurality of holes, the inner partition wall comprising:
a first naris conduit, the first naris conduit extending from the inner partition wall into the subject respiration space and into the subject oxygen reservoir and providing, through the inner partition wall, a bi-directional fluid flow channel between the subject respiration space and the subject oxygen reservoir, wherein when the mask is laid over the face of a subject, the first naris conduit is configured to be positioned in close proximity to the subject nares and wherein the closer the holes to the first naris conduit or to the second naris conduit, the smaller the holes; and
a first carbon dioxide conduit having a distal end that is connected to the first naris conduit and is in fluid flow communication with an interior space of the first naris conduit.

* * * * *